United States Patent
Guo

(10) Patent No.: US 10,022,141 B2
(45) Date of Patent: *Jul. 17, 2018

(54) METHOD AND APPARATUS FOR THREAD TRANSECTION OF A LIGAMENT

(71) Applicant: Joseph Guo, Monterey Park, CA (US)

(72) Inventor: Joseph Guo, Monterey Park, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/674,501

(22) Filed: Mar. 31, 2015

(65) Prior Publication Data

US 2015/0201959 A1    Jul. 23, 2015

Related U.S. Application Data

(60) Division of application No. 13/870,291, filed on Apr. 25, 2013, which is a continuation-in-part of
(Continued)

(51) Int. Cl.
*A61B 17/32* (2006.01)
*A61B 17/34* (2006.01)
(Continued)

(52) U.S. Cl.
CPC .... *A61B 17/320036* (2013.01); *A61B 17/149* (2016.11); *A61B 17/34* (2013.01);
(Continued)

(58) Field of Classification Search
CPC ........ A61B 2017/145; A61B 2017/146; A61B 17/14; A61B 17/148; A61B 17/32; A61B 17/320036; A61B 17/320016; A61B 17/32002; A61B 17/3205; A61B 17/3209; A61B 17/320092; A61B 17/32056;
(Continued)

(56) References Cited

U.S. PATENT DOCUMENTS 184,804 A    11/1876   Stohlmann
1,967,888 A    7/1934   Kearsley
(Continued)

FOREIGN PATENT DOCUMENTS

KR    1020110102818 A    9/2011
KR    1020120060054 A    6/2012
(Continued)

OTHER PUBLICATIONS

International Search Report, dated Feb. 24, 2015, 5 pages, from PCT/US14/18394, published as WO 2014/175957 on Oct. 30, 2014.
(Continued)

*Primary Examiner* — Elizabeth Houston
*Assistant Examiner* — Mohamed Gabr
(74) *Attorney, Agent, or Firm* — Fulwider Patton LLP

(57) ABSTRACT

A method and apparatus for transecting soft tissue, such as a ligament, and more particularly, the transverse carpal ligament. An hollow introducer needle and a threadlike cutting element enable the method to performed in a minimally invasive manner. The cutting element is routed into position about the target ligament such that the cutting element both enters and exits the body from the same side of the ligament. The substantially smooth exterior surface of the cutting element serves to provide for a kerf-less cut.

9 Claims, 16 Drawing Sheets

Related U.S. Application Data application No. 13/460,246, filed on Apr. 30, 2012, now Pat. No. 9,381,033.

(51) Int. Cl.
*A61B 17/14* (2006.01)
*A61B 17/3207* (2006.01)

(52) U.S. Cl.
CPC *A61B 17/3403* (2013.01); *A61B 2017/32006* (2013.01); *A61B 2017/320733* (2013.01)

(58) Field of Classification Search
CPC ...... A61B 17/3403; A61B 2017/32006; A61B 2017/320028; A61B 2017/320032; A61B 2017/32004; A61B 2017/320076; A61B 2017/320096; A61B 2017/320008; A61B 2017/320072; A61B 2017/32096; A61B 2017/320733; A61B 17/149; A61B 17/32075; A61B 17/320783; A61B 2017/320791
See application file for complete search history.

(56) References Cited

U.S. PATENT DOCUMENTS

| | | |
|---|---|---|
| 2,759,261 A | 8/1956 | Setecka |
| 3,494,490 A | 2/1970 | Shell |
| 3,650,274 A | 3/1972 | Edwards et al. |
| 4,425,706 A | 1/1984 | Southworth et al. |
| 4,538,611 A | 9/1985 | Kelman |
| 4,617,713 A | 10/1986 | Pomerenke |
| 4,672,734 A | 6/1987 | Kawada et al. |
| 4,773,421 A | 9/1988 | Davis |
| 4,962,770 A | 10/1990 | Agee et al. |
| 5,029,573 A | 7/1991 | Chow et al. |
| 5,273,024 A | 12/1993 | Menon et al. |
| 5,323,765 A | 6/1994 | Brown et al. |
| 5,334,214 A | 8/1994 | Putnam |
| 5,458,611 A | 10/1995 | Resnick et al. |
| 5,769,865 A | 6/1998 | Kermode et al. |
| 5,968,076 A | 10/1999 | Granger et al. |
| 6,346,106 B1 | 2/2002 | Jako |
| 7,637,883 B2 | 12/2009 | Nyi |
| 7,780,690 B2 | 8/2010 | Rehnke |
| 7,857,813 B2 | 12/2010 | Schmitz et al. |
| 8,062,300 B2 | 11/2011 | Schmitz et al. |
| 8,192,435 B2 | 6/2012 | Bleich et al. |
| 8,348,966 B2 | 1/2013 | McCormack et al. |
| 8,405,143 B2 | 3/2013 | Lin et al. |
| 8,419,728 B2 | 4/2013 | Klotz et al. |
| 8,444,658 B2 | 5/2013 | Kim |
| 8,454,654 B2 | 6/2013 | Ferragamo et al. |
| 8,561,616 B2 | 10/2013 | Rousseau et al. |
| 8,702,654 B2 | 4/2014 | Agee et al. |
| 8,753,364 B2 | 6/2014 | McCormack et al. |
| 8,992,424 B2 | 3/2015 | Orbay et al. |
| 2004/0107648 A1* | 6/2004 | Sung ............... B23D 61/185 51/295 |
| 2004/0143280 A1 | 7/2004 | Suddaby |
| 2004/0220604 A1 | 11/2004 | Fogarty et al. |
| 2006/0271080 A1 | 11/2006 | Suddaby |
| 2008/0033465 A1 | 2/2008 | Schmitz et al. |
| 2009/0048620 A1 | 2/2009 | Weiss et al. |
| 2009/0157124 A1 | 6/2009 | Ferragamo et al. |
| 2010/0331883 A1 | 12/2010 | Schmitz et al. |
| 2013/0165962 A1 | 6/2013 | Porshinsky et al. |
| 2015/0133982 A1 | 5/2015 | Park |

FOREIGN PATENT DOCUMENTS

| | | |
|---|---|---|
| KR | 1020120072966 A | 7/2012 |
| KR | 1020130038451 A | 4/2013 |

OTHER PUBLICATIONS

Interational Search Report, dated Jul. 11, 2013, 2 pages, from PCT/US13/38653, published as WO 2013/165900 on Nov. 7, 2013.
Journal of the Korea Society for Surgery of the Hand, Percutaneous Carpal Tunnel Release Using Preoperative Ultrasonography and the Wire Rope, Aug. 30, 2012, 8 pages.

* cited by examiner

METHOD AND APPARATUS FOR THREAD TRANSECTION OF A LIGAMENT

CROSS-REFERENCES TO RELATED APPLICATIONS

This application is a division of U.S. Ser. No. 13/870,291 filed Apr. 25, 2013, which is a continuation-in-part of U.S. Ser. No. 13/460,246, filed on Apr. 30, 2012, incorporated by reference herein in its entirety.

The present invention is generally directed to a surgical method and to an apparatus for performing such method. More particularly, the invention provides for the transection, by minimally invasive means, of a ligament such as for example the transverse carpal ligament that is commonly released as a treatment for carpal tunnel syndrome.

BACKGROUND

Many people suffer from injury to the soft tissues of the wrist and carpal tunnel, often caused by frequent, sustained repetitive motion involving the hands. Repetitive activities which require the same or similar hand/wrist action can result in injuries which have been collectively referred to as Cumulative Repetitive Stress Syndrome or Repetitive Strain Injury. The most familiar and common of such wrist injuries is known as carpal tunnel syndrome which produces pain, discomfort, nerve conduction disturbances, and impairment of function of the hand and sometimes the arm as well. The most common symptoms of this condition include intermittent pain and numbness of the hand.

Carpal tunnel syndrome occurs when the median nerve which runs from the forearm into the hand, becomes pressed or squeezed at the wrist. The median nerve provides feeling in one's thumb and along with index, middle and ring ringers. The median nerve controls sensations to the palmar side of the thumb and these fingers as well as impulses to some muscles in the hand which allow the fingers and thumb to move. The median nerve receives blood, oxygen and nutrients through a microvascular system which is present in the connective tissue surrounding the nerve fiber. Increased pressure on the nerve fiber can constrict these microvessels and will reduce the blood flow to the median nerve. Any prolonged deprivation of oxygen and nutrients can result in severe nerve damage.

The median nerve passes through the carpal tunnel, a canal in the wrist surrounded by the carpal bones on three sides and a fibrous sheath called the transverse carpal ligament on the fourth side. In addition to the median nerve, the nine flexor tendons in the hand pass through this canal. When compressed, the median nerve will cause pain, weakness or numbness in the hand and wrist which may also radiate up along he arm. The median nerve can be compressed by a decrease in the size of the carpal canal itself or an increase in the size of its contents (i.e. such as the swelling of the flexor tendons and of the lubrication tissue surrounding these flexor tendons), or both. For example, conditions that irritate or inflame the tendons can cause them to swell. The thickening of irritated tendons or swelling of other tissue within the canal narrows the carpal canal, causing the median nerve to be compressed. The cross-sectional area of the tunnel also changes when the hand and wrist changes positions. Wrist flexion or extension can decrease the cross-sectional area, thus increasing the pressure exerted on the median nerve. Flexion also causes the flexor tendons to somewhat rearrange which can also compress the median nerve. For example, simple bending of the wrist at a 90 degree angle will decrease the size of the carpal canal. Without treatment, carpal tunnel syndrome can lead to chronic neural muscular disorders of the hand and sometimes the arm.

Treatment for carpal tunnel syndrome includes a variety of non-surgical as well as surgical procedures, wherein carpal tunnel release is one of the most common surgical procedures that is performed. Such surgery involves the severing of the transverse carpal ligament to relieve the pressure on the median nerve and is commonly performed via either open or endoscopic methods. In open methods, the skin lying over the carpal tunnel is incised after which the transverse carpal ligament is transected under direct vision. The skin is then reapproximated with sutures. Endoscopic methods require incision of the skin in one or more locations to allow for the insertion of an endoscope along with various tools that are needed to transect the ligament. Such tools typically include a combination of a specially configured scalpel and guide instrument. The insertion of such tools into proper position below, above or both below and above the target ligament further requires the formation of one or more pathways in the hand with attendant trauma to the surrounding tissue and the potential for nerve damage as well as a more protracted post-surgical healing process. Additionally, the use of a scalpel typically requires multiple passes thereof in order to complete a transection which causes a complex pattern of cuts to be imparted onto the severed ligament surfaces.

Less invasive techniques have been proposed including for example the use of flexible saw elements that are introduced into the hand and positioned adjacent to or wrapped about a portion of the target ligament after which the saw element is reciprocated to cut the tissue. A substantial disadvantage of a cut that is made by a saw-like instrument as opposed to a knife-like instrument is inherent in the fact that a kerf is created. The material that is removed from the kerf is either deposited in and around the surgical site or additional steps must be taken to retrieve such material. Additionally, the cut surfaces that are created by a saw tend to be relatively rough and abraded with microtrauma on the cutting surface that may increase inflammatory response (edema, erythema, heat and pain), could result in local tissue adhesions and scarring which can delay or complicate the healing process.

Alternatively, techniques have been proposed wherein a taut wire, string or filament is used to cut a ligament. The cut is achieved either by the tautening of the cutting element or alternatively, by reciprocating the taut element. Disadvantages associated with such an approach are inherent in the less than optimal geometry by which a taut wire can be brought to bear on the target ligament and by the invasiveness of the tightening apparatus.

A new method and apparatus is needed with which tissue such as a ligament can be percutaneously accessed and transected so as to cause a very minimal amount of disruption to the surrounding tissue and by which a smooth, kerf-less cut is achieved.

SUMMARY OF THE INVENTION

The present invention provides for the minimally-invasive transection of tissue such as a ligament. The method and apparatus obviate the need for any incisions, minimizes disruption of the tissue surrounding the target ligament, enables a smooth kerf-less cut of the target ligament to be achieved, requires no suturing and can be easily and quickly performed in a clinic setting.

More particularly, the invention provides for the introduction of a thin and flexible thread-like cutting element into the body and its routing about the target ligament. Subsequent manipulation of the protruding ends of the smooth cutting element serves to transect the ligament by a smooth kerf-less cut. A routing tool component of the invention enables the cutting element to be easily and quickly introduced and routed into position about the target ligament with minimal disruption or trauma to the surrounding tissue. The routing tool component may take the form of a hollow introducer needle or a specially configured hooked retrieval needle comprising a thin, rigid and elongated needle-like element having near its distal end a hook-like feature formed therein that is dimensioned to engage the cutting element and configured to maintain engagement therewith when being pulled proximally.

In the transection of the transverse carpal ligament, the routing tool component is initially used to puncture the skin of the hand so as to form a first access port at a location proximal to the ligament and laterally adjacent thereto. The tool is then extended into the hand through the carpal tunnel along a path immediately below the ligament and is caused to emerge from the hand through a second access port formed thereby just distal to the ligament. The position of the routing tool in the hand and especially in relation to the ligament is preferably visualized throughout the placement procedure using for example an ultrasound imaging device to enable precise maneuvering of the tool.

Should a hooked retrieval needle serve as the routing tool and once it is in the position within the hand as is described above, a length of the cutting element is engaged by the hooking element of the retrieval needle and a loop thereof is drawn into the hand via the second access port. The zero bend radius of the cutting element allows the loop that is formed to be as compact as possible. The loop is drawn under the ligament and out of the first access port where it is disengaged from the retrieval needle and its free end pulled through. Reextension of the retrieval needle into the hand and along the top surface of the ligament to the second access port allows a second length of the cutting element to be engaged and a loop thereof drawn into the hand, over the ligament and out of the first access port. By pulling the second free end of the cutting element through the hand over the ligament and out of the first access port, the routing of the cutting element about the ligament is complete leaving the cutting element in position for the transection.

Should a hollow introducer needle serve as the router tool, the cutting element is inserted into the needle's proximal end while the needle is in the position described above. The cutting element is extended through the length of the needle and approximately one half of the cutting element is pulled from the distal end of the needle. The needle is then proximally retracted from the hand to leave the cutting element in place in the hand such that a sizable portion thereof protrudes from the first access port as well as from the second access port. The hollow needle is then reinserted into the first access port and adjacent to the proximally protruding length of cutting element, is extended through the hand immediately above the ligament and out of the second access port. The distally protruding portion of the cutting element is then fed into the distal end of the hollow needle in place within the hand and extended through its length so as to emerge from the proximal end of the needle after which the needle is retracted from the hand. The routing of the cutting element about the ligament is thereby complete leaving the cutting element in position for the transection. Alternatively, one end of the cutting element may be initially introduced into the distal end of the needle and extended there through. After retraction of the needle and reinsertion into and through the hand above the ligament, the second end of the cutting element is introduced into the distal end of the needle and fed there through. Retraction of the needle leaves the cutting element in place for the transection. As a further alternative, the needle may be reinserted into the hand via the second access port.

The physical characteristics of the cutting element are selected to facilitate a kerf-less cut through the ligament. The small diameter and high tensile strength of the cutting element provides for the transection of the ligament by the manipulation of the ends of the cutting element. Unequal forces can alternatingly be applied to the two ends of the cutting element to induce a reciprocating cutting action. Alternatively, one end can be pulled with greater force than the other element so as to pull the cutting element in a single direction as it cuts through the ligament. As a further alternative, both ends can be pulled simultaneously with equal force to simply pull the cutting element through the ligament. The substantially smooth, none abrasive surface of the cutting element causes a knife-like cut to be achieved without the formation of a kerf and thus without an attendant deposition of detached material in and about the surgical site. Reciprocation may preferably be achieved with the use of a power tool, by which the two ends of the cutting element are alternating pulled. A stiffened section one or both ends of the cutting element facilitates the introduction of the cutting element into the hollow introducer needle.

The very small cross-section of the routing tool, whether it takes the form of the hollow introducer needle or the hooked retrieval needle, and of the cutting element, as well as minimally invasive method by which such hardware is introduced and positioned within the hand greatly reduces the risk of injury to the median nerve as well as to the smaller nerves that branch out therefrom. Additionally, the fact that the cutting element is positioned via only two tiny punctures and that the transection is performed via only one of those punctures, recovery time is minimal and scaring is essentially negligible.

The invention can additionally be modified in order to further simplify the surgical procedure. For example the sequence of steps can altered in the routing of the cutting element about the ligament such that the routing tool is first extended across the top of the ligament before the tool is subsequently extended through the carpal tunnel for the routing of the cutting element about the ligament. Additionally, a rigid alignment tool may be attached to the second end of the cutting element to facilitate engagement of the cutting element by the hooked retrieval needle embodiment of the routing tool component at a location completely within the hand and thus much closer to the distal edge of the ligament in order to minimize the transection of any tissue adjacent to the ligament. A retrieval needle may further be marked so as to allow the rotational orientation of the hooking element to be ascertained while within the hand and thereby enhance the ability to engage the cutting element. Additionally, a protective sleeve about a portion of the cutting element may be employed to protect tissue located between the proximal entry port and the ligament. Both ends of the cutting element may be caused to extend through a single sleeve or each end may be caused to extend about its own protective sleeve.

These and other advantages of the present invention will become apparent from the following detailed description of preferred embodiments which, taken in conjunction with the drawings illustrate by way of example the principles of the invention.

DETAILED DESCRIPTION OF THE PREFERRED EMBODIMENTS

The present invention provides for the minimally invasive transection of tissue and obviates the need for scalpels, saws or endoscopes. The invention is especially applicable for the transection of ligaments and most particularly, for the release of the transverse carpal ligament in the treatment of carpal tunnel syndrome.

Figure 1:
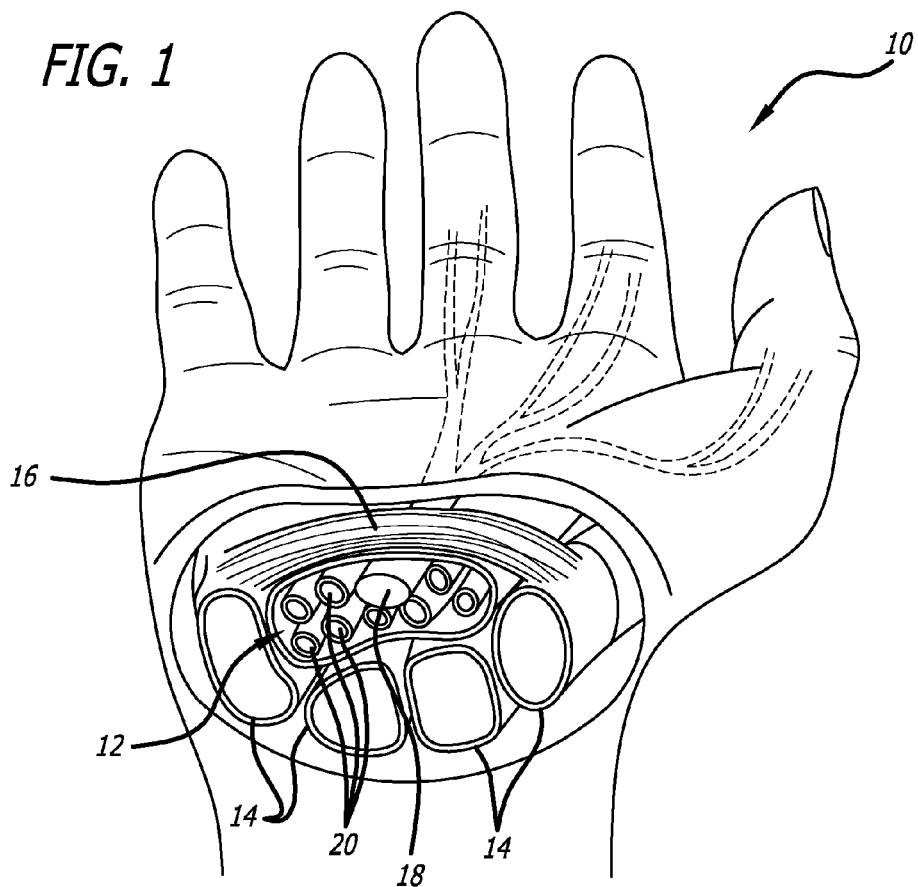
FIG. 1 is a cross-sectional view of the carpal tunnel area of the hand.

FIG. 1 is a cross-sectional view of the carpal tunnel area of the hand 10. The carpal tunnel 12 is the area of the wrist and palm of the hand 10 formed by a U-shaped cluster of bones 14 that form a hard floor and two walls of the tunnel. The roof of the tunnel is formed by the transverse carpal ligament 16 which attaches to the wrist bones. Within the confines of the tunnel is the median nerve 18 and the flexor tendons 20 of the thumb and fingers. Carpal tunnel syndrome is caused by a compression of the median nerve by either a decrease in the size of the tunnel or an increase in the size of its contents. Such pressure may be relieved by a release of the ligament such as by a transection thereof.

Figure 2:
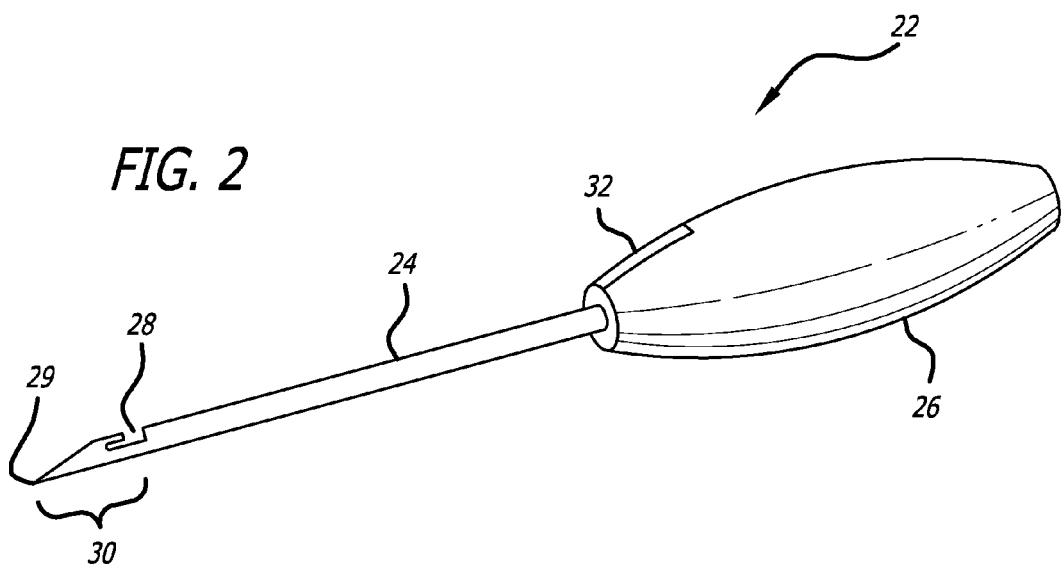
FIG. 2 is a perspective view of a preferred embodiment of the routing tool component of the present invention in the form of a hooked retrieval needle.

FIG. 2 is perspective view of a preferred embodiment of the routing tool of the present invention wherein such tool takes the form of a hooked retrieval needle 22. The tool generally includes a thin, rigid and elongated distal section 24 and a handle 26 at its proximal end. The distal section has hooking element 28 disposed near its distal end 30. The hooking element is preferably defined by a void formed within the outer diameter of the elongated distal section of the retrieval tool so as to present a substantially smooth outer surface and thereby minimize the potential for trauma as the tool is extended into or retracted from tissue. The distal end may have a sharp tip 29 as is shown in the illustrated embodiment. Alternatively, the tip may have a more blunted configuration. The hooking element is spaced slightly back (reference numeral 30) from the distal end. A marking 32 on the handle may be included demarking the rotational position of the hook-like feature near the tool's distal end. The length of the distal section is selected to be greater than the width of the transverse carpal ligament. Its diameter is selected to be no greater than about 1 mm.

Figure 3:
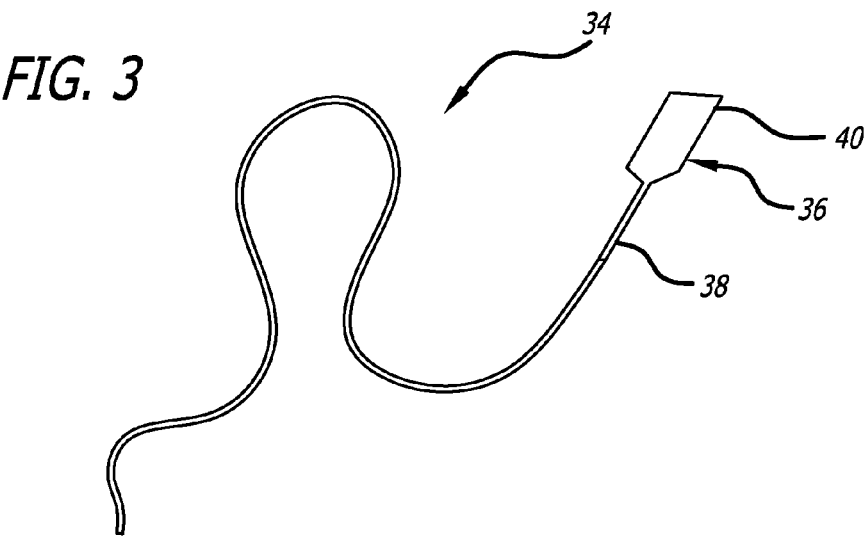
FIG. 3 is a perspective view of a preferred embodiment of the cutting element of the present invention.

FIG. 3 is a perspective view of the cutting element 34 of the present invention with the optional locator tool 36 attached thereto. The cutting element has a flexible, small diameter, thread-like structure with a high tensile strength and a smooth surface, preferably with an average surface roughness no greater than 50 micrometers. The cutting element may comprise a monofilament or a plurality of braided or otherwise joined fibers or strands wherein each strand has a smooth surface so as to present a relatively smooth, none-abrasive surface. Its physical characteristics include a bend radius of less than half the thickness of the ligament and preferably a zero bend radius, a diameter of less than about 1.0 mm, and a breaking strength of over 2 lbs. The cutting element may comprise fiber or yarn formed of cotton, silk, glass fiber, carbon fiber, various plastic fibers or metal. More particularly, textile fiber, synthetic fiber, mineral fiber, polymer fiber, microfibers may be used. The optional locator tool includes a rigid distal end 38 of a diameter sufficiently small to be extended into the access port and to be captured within the hooking element 28 of the retrieval tool 22. A handle 40 is disposed near its proximal end to enable the tool to be grasped and manipulated.

Figure 4A:
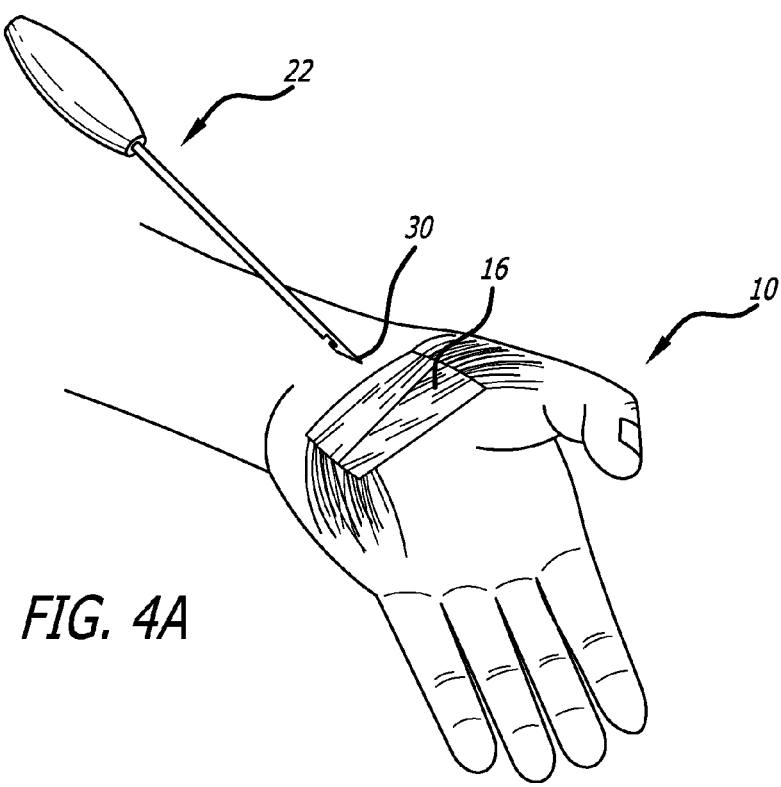
FIGS. 4A-H are cross-sectional views of the hand with a revealed transverse carpal ligament illustrating a preferred sequence of steps for practicing the method of the present invention using a hooked retrieval needle as the routing tool component.

FIGS. 4A-4H illustrate a preferred method of practicing the present invention. After anesthetizing the area of the hand 10 near and about the transverse carpal ligament 16, the distal end 30 of the retrieval needle 22 is brought into contact with the hand just proximal to the proximal edge of the target ligament as is shown in FIG. 4A. The ligament is visible in the Figures for purposes of clarity only as no incision is made throughout the entire procedure in any way expose the ligament to view. Additionally, an imaging device, such as an ultrasound device, such as is commonly used for a variety of imaging applications, is used to visualize the position of the retrieval needle relative to the ligament but is not shown so as not to obscure the surgical site again for purposes of clarity. It is preferable to enter the hand at a position about 30 mm proximal of the proximal edge of the transverse carpal ligament as the carpal tunnel can then be entered at a shallower angle obviating the need to adjust the angel of the needle after the tunnel has been reached and thereby minimizing trauma to tissue in addition to allowing the retrieval needle to be more easily imaged.

Figure 4B:
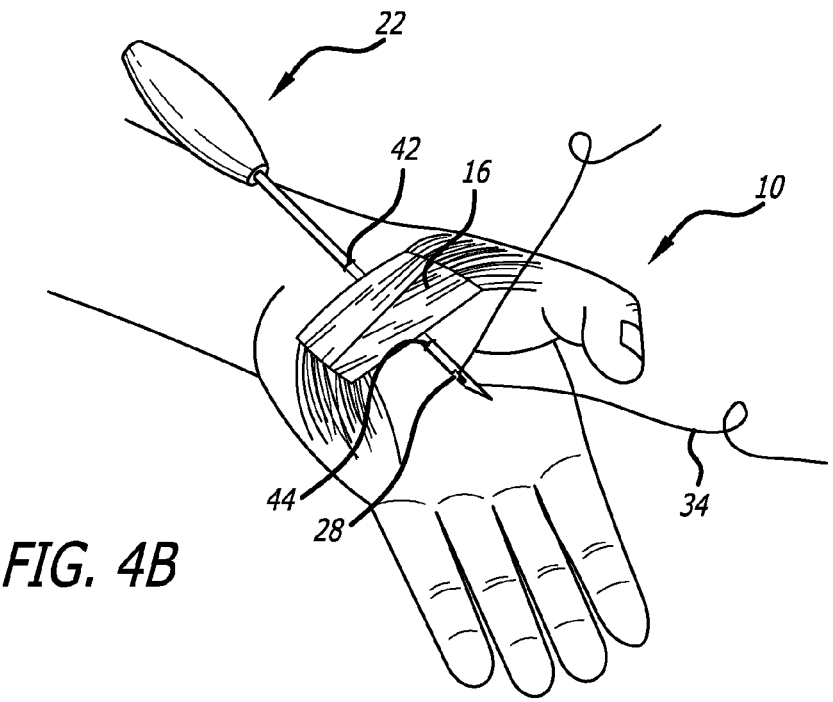

In FIG. 4B, the retrieval needle has been advanced into the hand via entry port 42, through the carpal tunnel just under the ligament and out through exit port 44. The entry and exit ports may be formed by the direct extension of the retrieval needle through the skin in the event the retrieval needle 22 is selected to have a sharp distal tip 29. In the event a retrieval tool is used with a blunt tip, a sharp instrument is necessary for forming the access ports and guide the retrieval tool into the hand. The Figure additionally shows the cutting element 34 having been engaged in the hooking element 28 near the tool's distal end. In this particular embodiment, the cutting element is devoid of a locator tool attached to its distal.

Figure 4C:
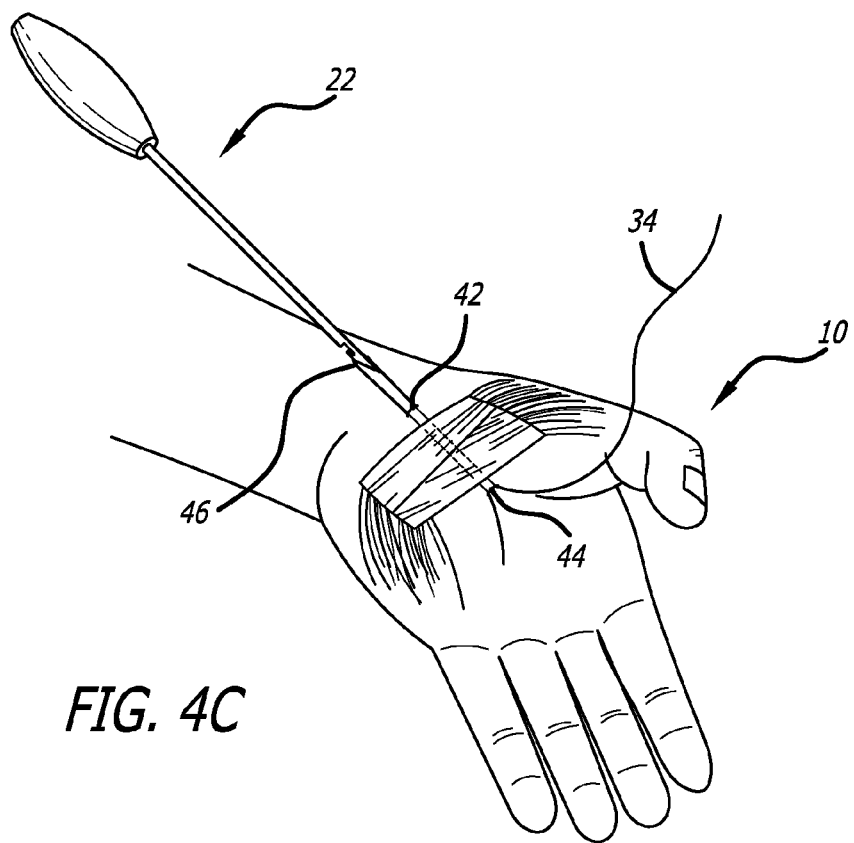
Figure 4D:
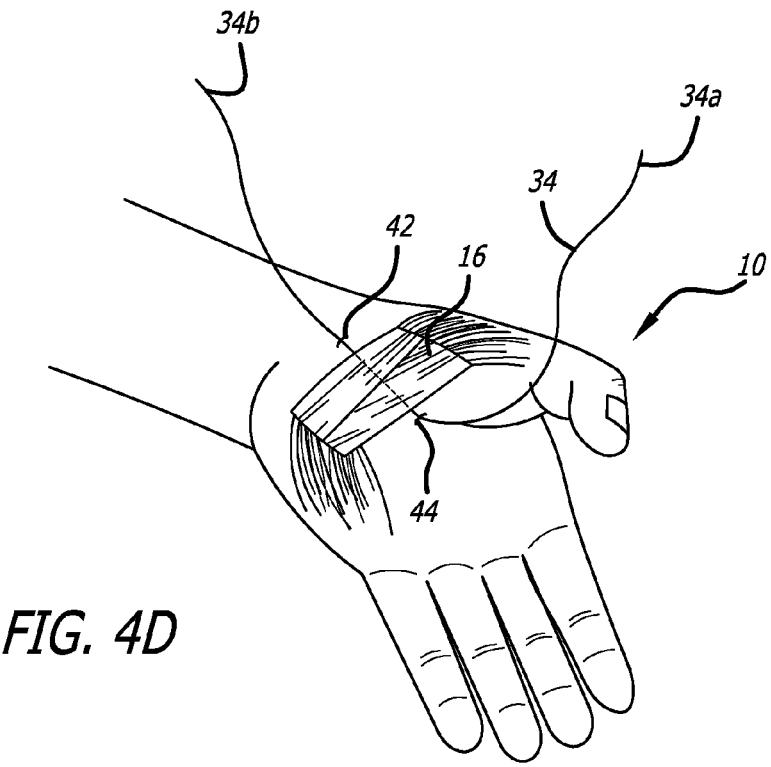

Once the cutting element 34 is engaged, the retrieval needle 22 is retracted from the hand so as to draw a loop 46 of the cutting element into the hand via port 44, through the carpal tunnel and out of entry port 42 as is shown in FIG. 4C. The loop is then disengaged from the retrieval needle and while one end of the cutting element 34*a* is restrained, the loop is pulled so as to draw the opposite end 34*b* of the cutting element free of the hand as is shown in FIG. 4D.

Figure 4E:
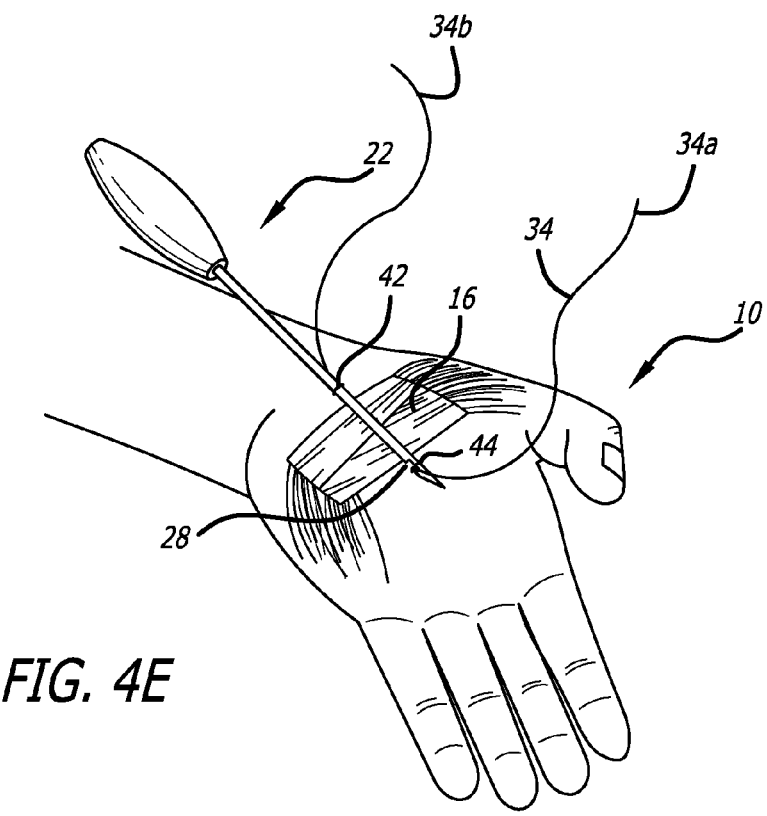

FIG. 4E illustrates the subsequent step of the method wherein the retrieval needle 22 is readvanced into the hand via access port 42, is guided across the top surface of ligament 16 to remerge from the hand via access port 44. The section of cutting element 34 extending from under the ligament is engaged with the hooking element 28 of the retrieval needle.

Figure 4F:
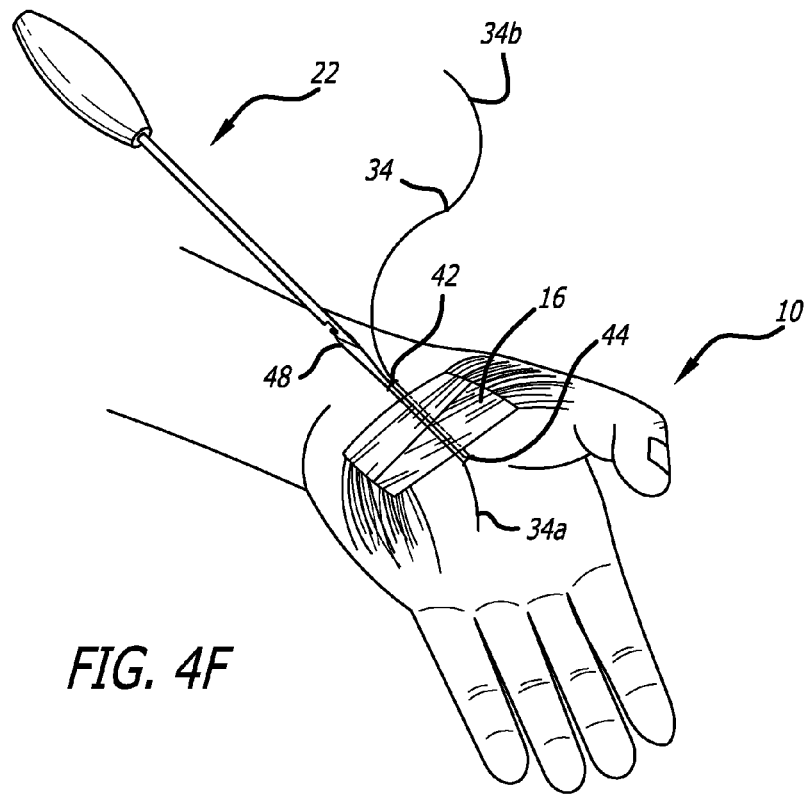
Figure 4G:
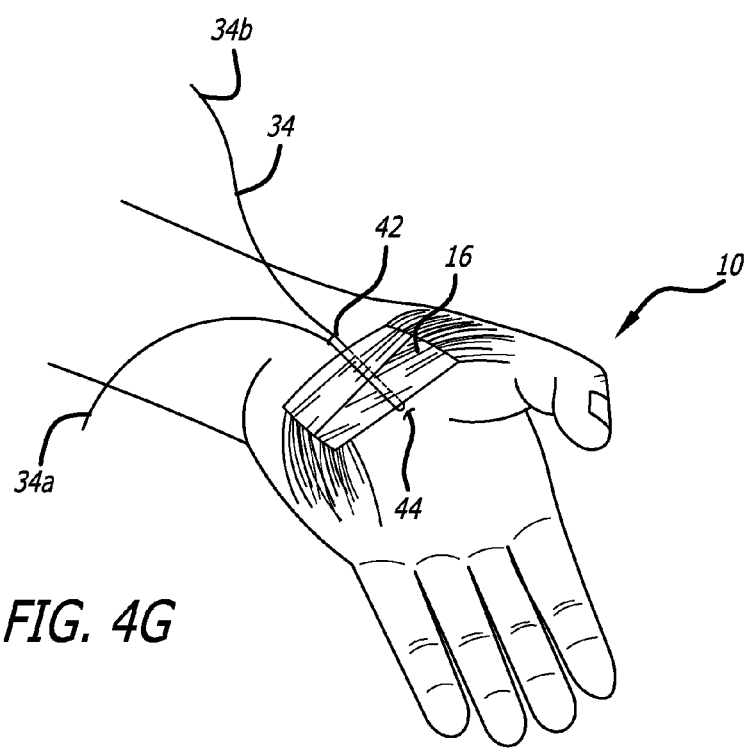
Figure 4H:
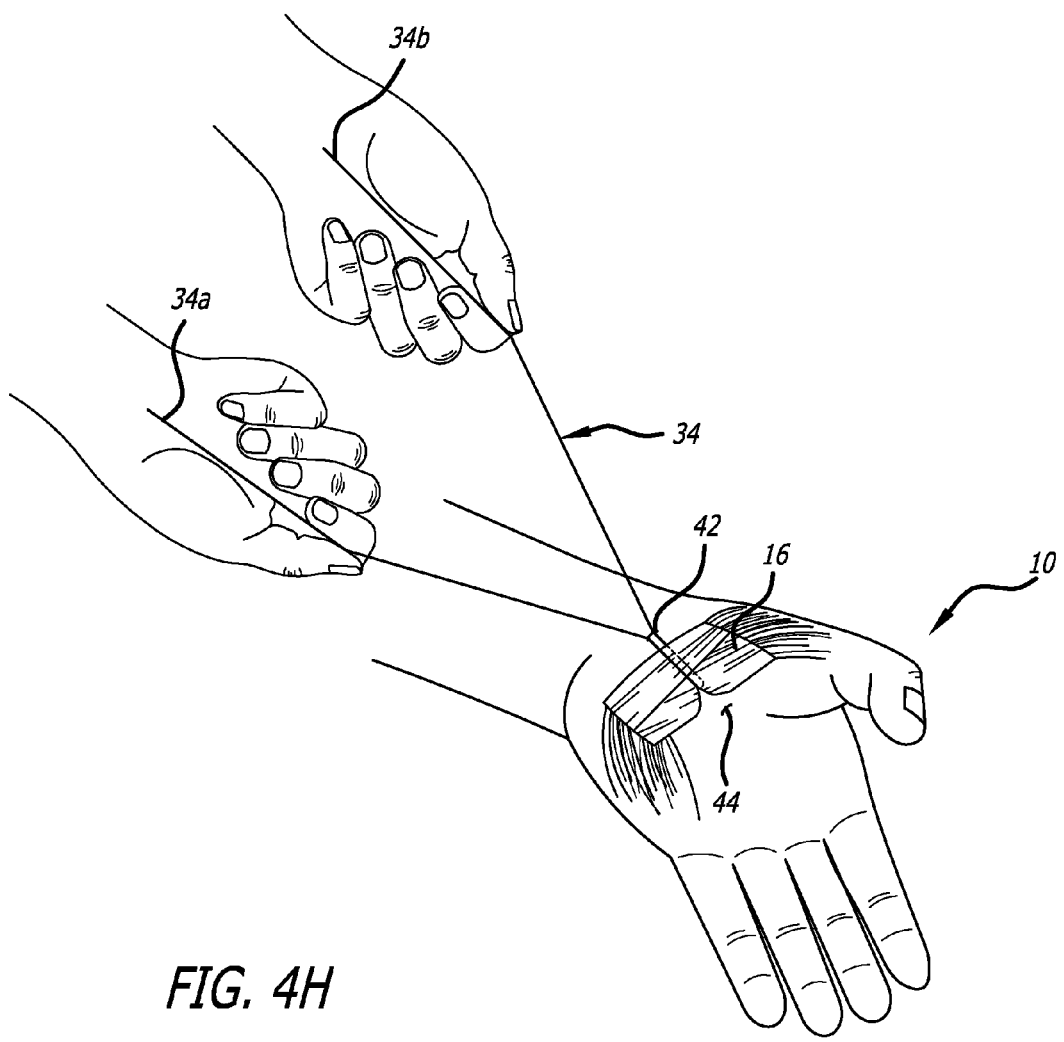

Once the cutting element 34 is again engaged, the retrieval needle 22 is retracted from the hand so as to draw a loop 48 of the cutting element into the hand via port 44, through the carpal tunnel and out of entry port 42 as is shown in FIG. 4F. The loop is then disengaged from the retrieval needle and while end 34*b* of the cutting element is restrained, the loop is pulled so as to draw the end 34*a* of the cutting element free of the hand as is shown in FIG. 4G. The cutting element is thereby in position about ligament 16 for subsequent manipulation to effect the transection. As is shown in FIG. 4H, the ends 34*a*, 34*b* of the cutting element may simply be grasped by the user, may be wound around the hands or fingers of the user for a firmer grip or alternatively, may be fitted with handles to provide for maximum grip and control. Unequal forces can alternatingly be applied to the two ends of the cutting element to induce a reciprocating cutting action either by hand or with the use of an appropriately configured power tool. Alternatively, one end can be pulled with greater force than the other element so as to pull the cutting element in a single direction as it cuts through the ligament. As a further alternative, both ends can be pulled simultaneously with equal force to simply pull the cutting element through the ligament. When transection has been achieved, the cutting element is simply withdrawn through access port 42. Application of a small bandage over each of the access ports 42, 44 completes the procedure.

Figure 5A:
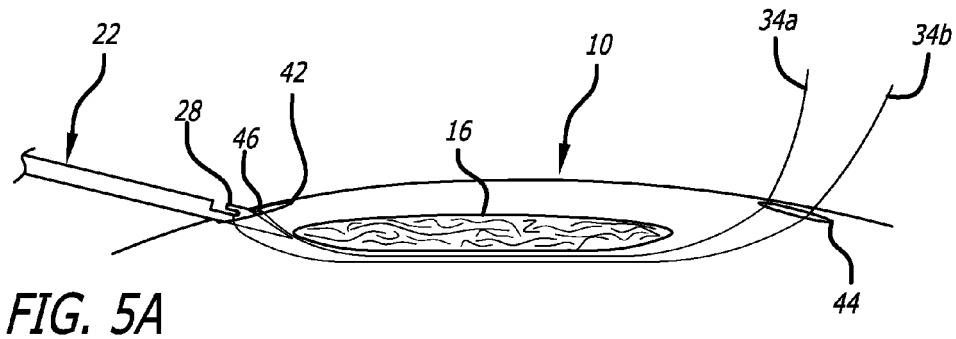
FIGS. 5A-C are cross-sectional views of the hand and the transverse carpal ligament illustrating alternative preferred steps for practicing the method of the present invention.

In an alternative embodiment, and as a modification to the step shown in FIG. 4C, the retrieval needle 22 is not completely withdrawn from access port 42 as illustrated in FIG. 5A. The needle is retracted just enough to expose the hooking element 28 and allow the loop 46 of the cutting element 22 to be disengaged and withdrawn, while most of the distal end 30 remains below the skin. As a result, it is more likely that the needle will follow the same pathway to the ligament 16 before traversing its top surface resulting in less trauma and disruption to intervening tissue both while advancing the needle as well as at the completion of the transection step.

Figure 5B:
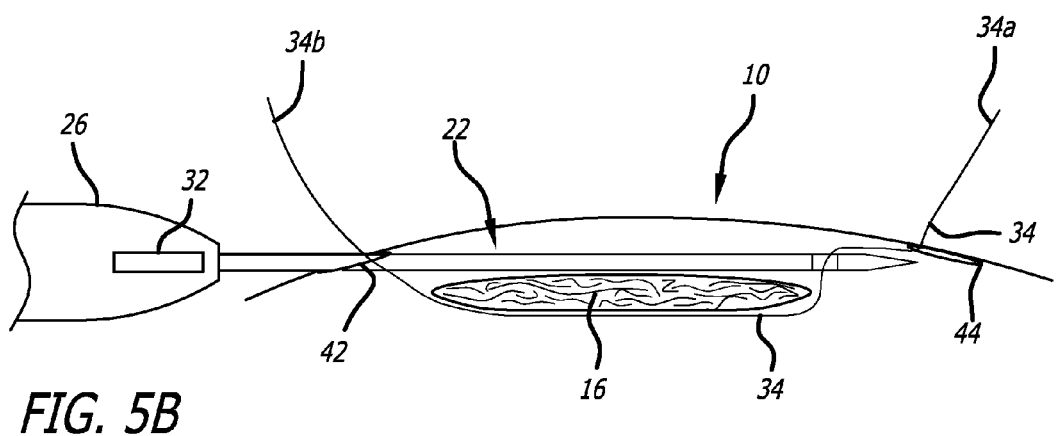

In another alternative embodiment, and as a modification of the step shown in FIG. 4E, the retrieval needle 22 is not extended through port 44 to engage cutting element 34 as is illustrated in FIG. 5B. Rather the cutting element is engaged within the hand, preferably as close to possible to the distal edge of the transverse carpal ligament 16. The needle is shown with its hooking element rotated toward the viewer. The marking 32 on the handle 26 allows the user to ascertain the rotational orientation of the hooking element without a direct view of the distal end of the retrieval needle. By engaging the cutting element 34 closer to the distal edge of the ligament before drawing it across the top surface of the ligament, less extraneous tissue is apt to be captured between the cutting element and the ligament and thus less trauma thereto will be caused during the transection of the ligament.

Figure 5C:
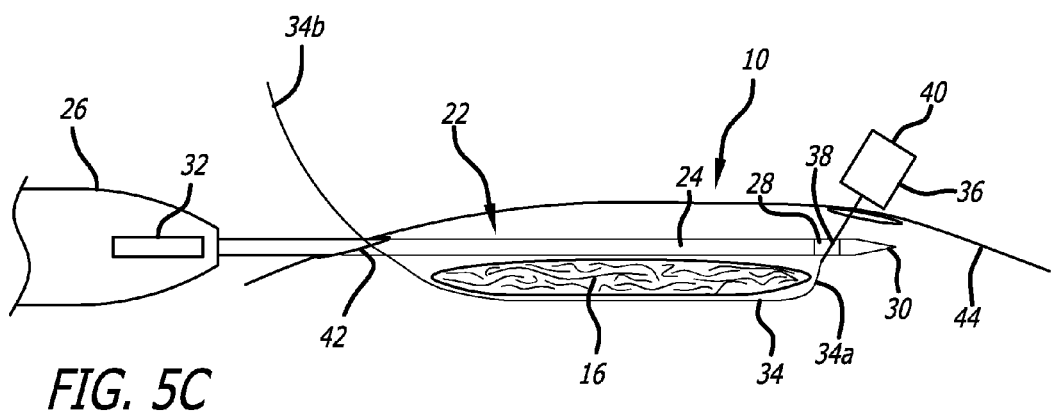

As a further alternative to the preferred embodiment shown in FIG. 5B, FIG. 5C illustrates the step using the cutting element 34 having the locator tool 40 attached thereto. Once the distal end 30 of the tool is in position such that the hooking element is located just distal of the distal edge of the transverse carpal ligament as confirmed by the ultrasound image, the cutting element 34 is pulled from the end 34*b* projecting from access port 42 so as to draw its opposite end 34*a* and the locator tool that is attached thereto into access port 44. Once the locator tool is extended to the approximate depth that is illustrated, the ability to more readily engage the retrieval needle is enhanced by virtue of the locator tool's visibility under ultrasound imaging and by virtue of the tactile feedback that is provided when contact is made between the rigid distal section 24 of the retrieval needle and the rigid distal end 38 of the locator tool. Once engagement with the hooking element 28 of the retrieval needle is confirmed, the locator tool is withdrawn from access port 44, leaving the cutting element in place within the hooking element. Subsequent retraction of the retrieval needle causes a loop of the cutting element to be drawn through the pathway above the ligament and out of access port 42. Severing the cutting element from the locator tool allows the free end 34*a* of the cutting element to be drawn through the hand and out of the access port to complete the routing of the cutting element about the target ligament.

In the event a cutting element 34 is selected that has a larger than zero bend radius, it may be desirable to first introduce a zero bend radius pilot thread into the hand and position it about the ligament in the manner as was described above with regard to placement of the actual cutting element. Once such pilot thread is in place, one end is attached directly to one end of the cutting element and simply pulled through so as to replace the pilot thread with the cutting element. Such approach allows the size of the access ports to be minimized that would otherwise have to be enlarged in order to accommodate the larger loops 46, 48 that are formed by a cutting element having a non-zero bend radius.

Figure 6A:
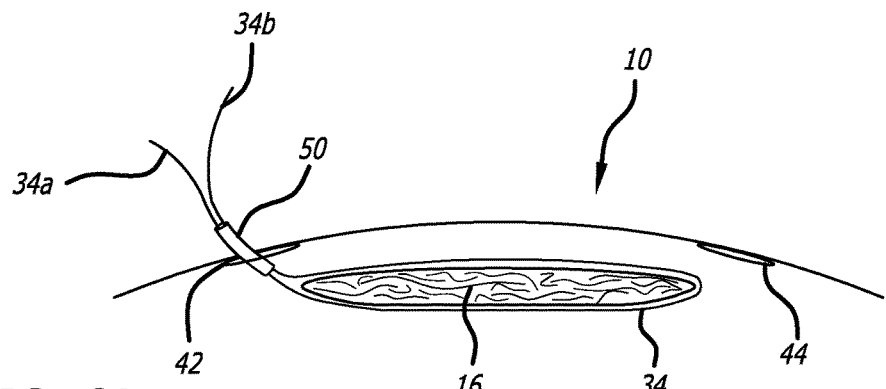
FIGS. 6A and B are cross-sectional views of the hand and the transverse carpal ligament illustrating an alternative preferred embodiment in which protective tubes are used.
Figure 6B:
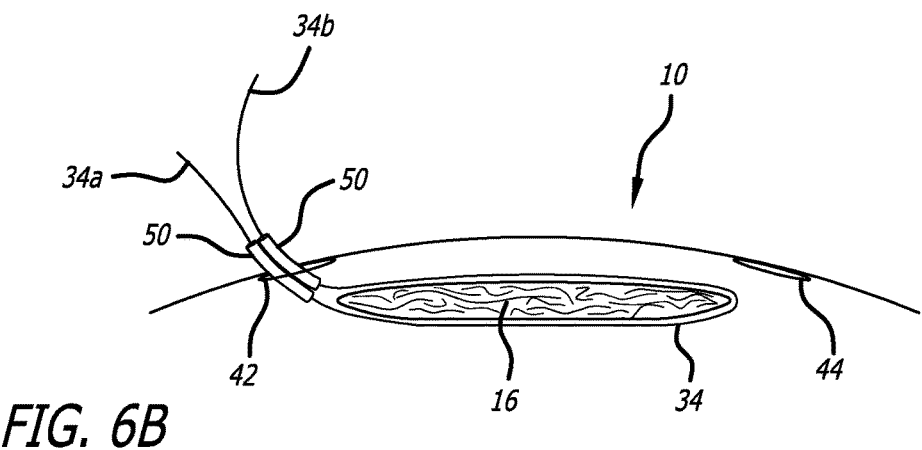

A further alternative preferred method of practicing the present invention includes the use of protective tube or tubes 50 that are positioned about the cutting element at access point 42 as is illustrated in FIGS. 6A and B. Both ends of the cutting element may be passed through a single tube (FIG. 6A) or each end may be passed through its own tube (FIG. 6B). The tube or tubes serve to protect the surrounding tissue from injury as tension is applied to the cutting element and it is drawn or reciprocated to effect the transection. The tubes are especially effective when the cutting element undergoes some curvature in and about access point 42. The thin-walled tubing is selected to be flexible but resistant to being cut by the cutting element.

Figure 7A:
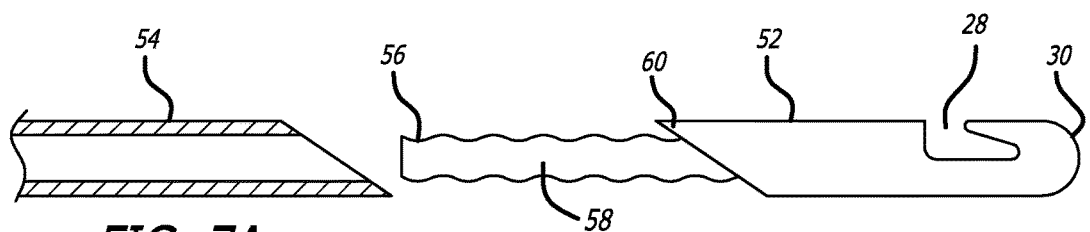
FIGS. 7A and 7B are greatly enlarged cross-sectional views of an alternative preferred embodiment of the hooked retrieval needle.
Figure 7B:
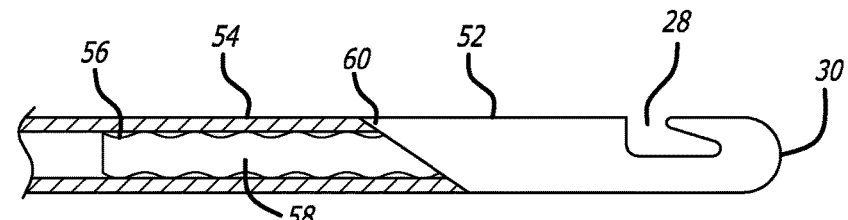

In another alternative preferred embodiment, a modified retrieval tool 52 is configured for capture within a hypodermic needle 54 as is shown in FIGS. 7A and 7B. The hypodermic needle is initially used to form access port 42, to inject anesthetic and/or a liquid, such as saline solution, to inflate the surgical site so as to separate the various tissues and components to provide easier access for routing the cutting element into place. After the injection is complete, the hypodermic needle is extended out of the body to form access port 44. The specially configured blunt tipped retrieval tool is inserted into the hypodermic needle and locked into place (FIG. 7B) via locking mechanism 56. Such locking mechanism may take any of various forms including the interference fit that is created by the slightly wavy configuration of the shank 58 that is shown in the Figure. After the cutting element is engaged by the hooking element 28 of the retrieval tool, the hypodermic needle is retracted to draw loop 46 into the hand as is shown in FIG. 4C. The distal section 60 of the retrieval tool 52 may have its outer diameter selected to substantially match the outer diameter of the hypodermic needle to create a smooth transition.

Figure 8:
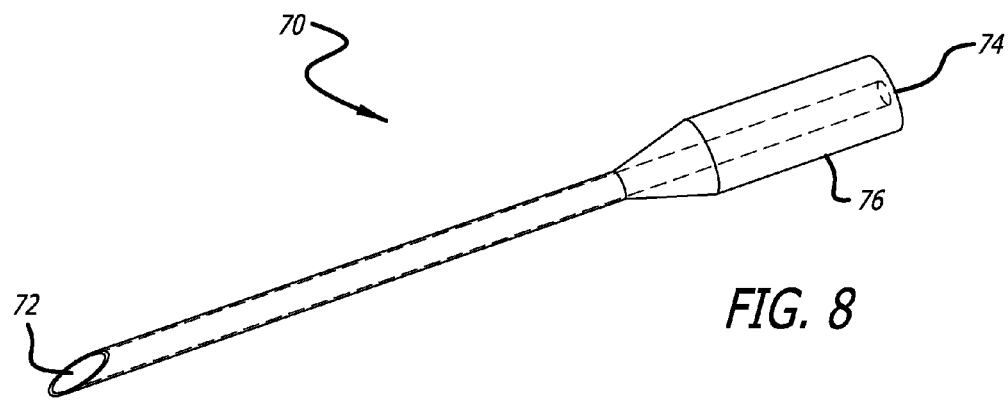
FIG. 8 is a perspective view of another preferred embodiment of the routing tool component of the present invention in the form of a hollow introducer needle.

FIG. 8 is perspective view of another preferred embodiment of routing tool component of the present invention wherein the tool takes the form of a hollow introducer needle 70. The hollow needle includes a sharp or blunt distal end 72 and has hollow interior extending from its distal end to its proximal end 74. A handle 76 may be disposed about its proximal section to facilitate its manipulation. The length of the section of introducer needle distal to the handle is selected to be greater than the width of the target transverse carpal ligament. Its diameter is selected to be no greater than about 2 mm.

Figure 9:
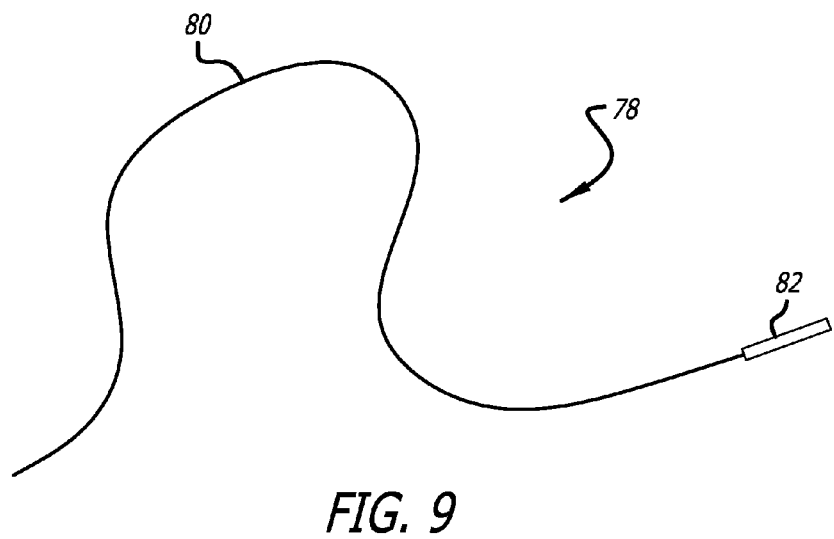
FIG. 9 is a perspective view of another preferred embodiment of the cutting element of the present invention.

FIG. 9 is a perspective view of a preferred embodiment of the cutting element 78 of the present invention. Substantially the entire length 80 of the cutting element has a flexible, small diameter, thread-like structure with a high breaking strength and a smooth surface, preferably with an average surface roughness no greater than 50 micrometers. The cutting element may comprise a monofilament or a plurality of braided, twisted or otherwise joined fibers or strands wherein each strand has a smooth surface so as to present a relatively smooth, none-abrasive surface. Its physical characteristics include a bend radius of less than half the thickness of the ligament and preferably a zero bend radius, a diameter of less than about 1.0 mm, and a breaking strength of over 2 lbs. The cutting element may comprise fiber or yarn formed of cotton, silk, glass fiber, carbon fiber, various plastic fibers or metal. More particularly, textile fiber, synthetic fiber, mineral fiber, polymer fiber, microfibers may be used. At least one end of the cutting element has a stiffened section 82 to facilitate the introduction into and the extension through the hollow introducer needle. 70. The stiffened section may be formed by covering the section with relatively stiff tubing, by subjecting a synthetic fiber to heat, by the infusion of for example a resin or by the attachment of for example a suture needle. The stiffened section 82 preferably has a diameter less than the inner diameter of the introducer needle. The enhanced diameter shown in the drawing is for illustration purposes only.

Figure 10A:
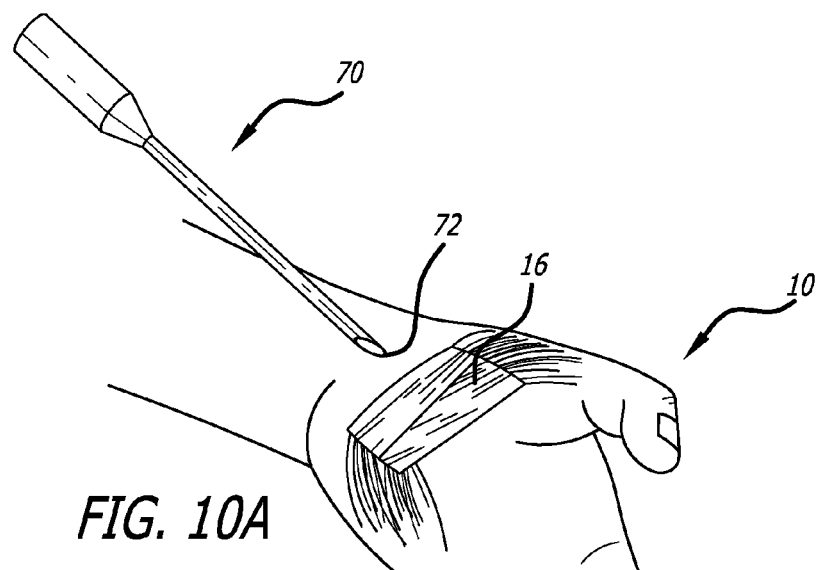
FIGS. 10A-J are cross-sectional views of the hand with a revealed transverse carpal ligament illustrating a preferred sequence of steps for practicing the method of the present invention using a hooked retrieval needle as the routing tool component.

FIGS. 10A-J illustrate a preferred method of practicing the present invention. After anesthetizing the area of the hand 10 near and about the transverse carpal ligament 16, the distal end 72 of the hollow introducer needle 70 is brought into contact with the hand just proximal to the proximal edge of the target ligament as is shown in FIG. 10A. The ligament is visible in the Figures for purposes of clarity only as no incision is made throughout the entire procedure to in any way expose the ligament to view. Additionally, an imaging device, such as an ultrasound device, such as is commonly used for a variety of imaging applications, is used to visualize the position of the introducer needle relative to the ligament but is not shown so as not to obscure the surgical site again for purposes of clarity. It is preferable to enter the hand at a position about 30 mm proximal of the proximal edge of the transverse carpal ligament as the carpal tunnel can then be entered at a shallower angle obviating the need to adjust the angel of the needle after the tunnel has been reached and thereby minimizing trauma to tissue in addition to allowing the introducer needle to be more easily imaged.

Figure 10B:
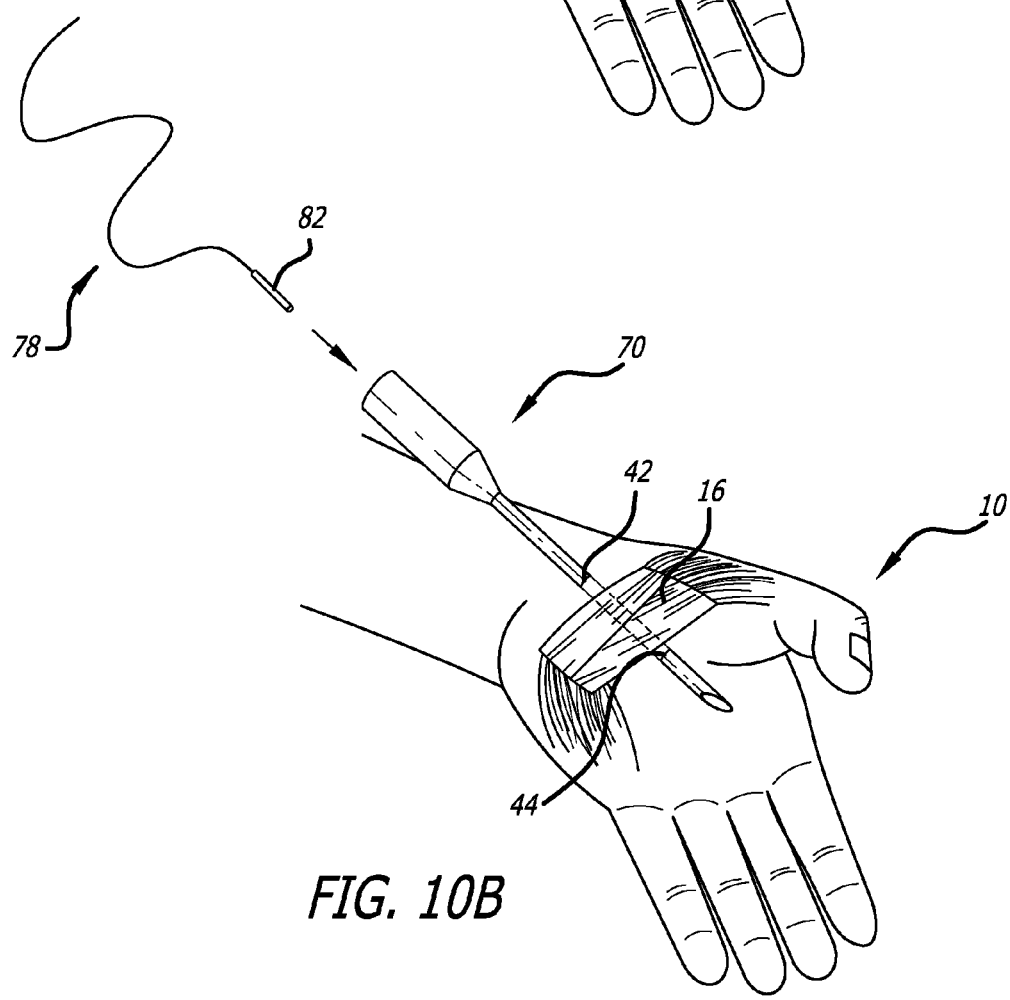

In FIG. 10B, the introducer needle has been advanced into the hand via entry port 42, through the carpal tunnel just under the ligament and out through exit port 44. The entry and exit ports may be formed by the direct extension of the introducer needle through the skin. The Figure additionally shows the cutting element 78 being advanced toward the proximal opening of introducer needle wherein the stiffened section 82 of the cutting element serves to facilitate the threading of the cutting element into the needle's hollow interior.

Figure 10C:
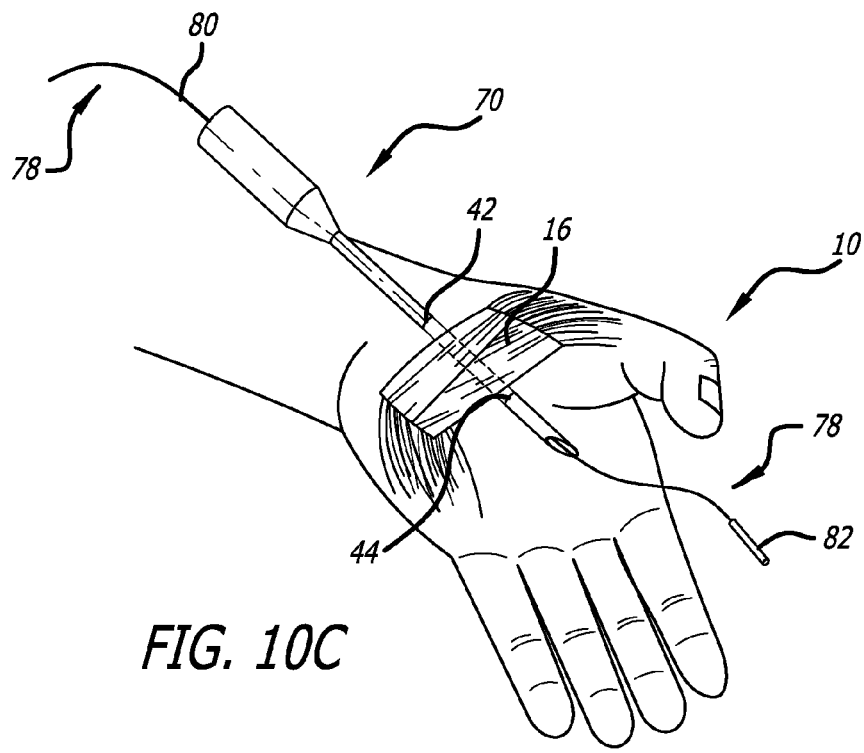
Figure 10D:
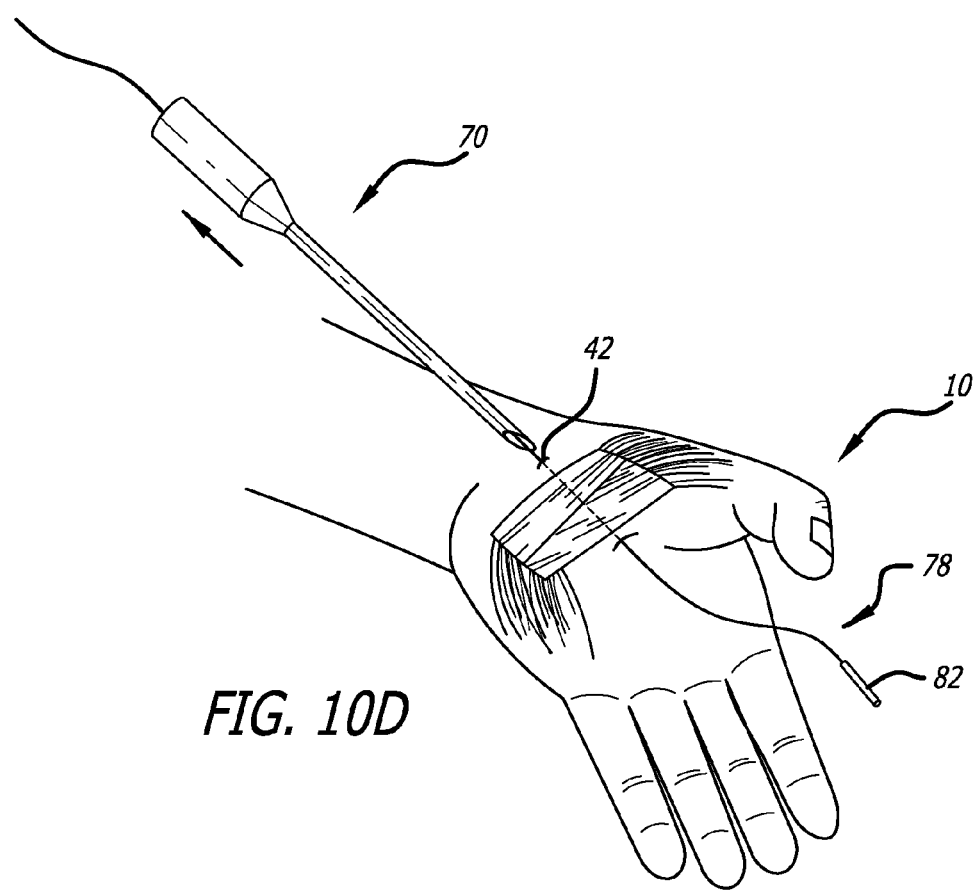
Figure 10E:
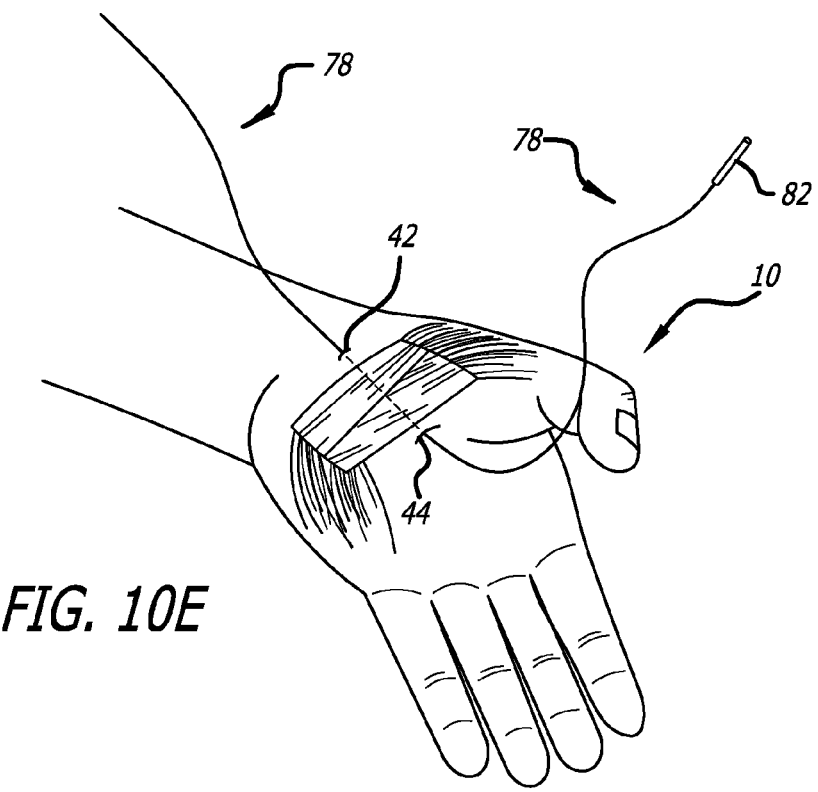

FIG. 10C shows the cutting element emerging from the introducer needle's distal end while FIG. 10D illustrates the subsequent retraction of the needle to leave the cutting element in place as is shown in FIG. 10E. As such, a section of cutting element 78 is left projecting from entry port 42 and from access port 44 while its central section extends through the carpal tunnel just below the transverse carpal ligament 16.

Figure 10F:
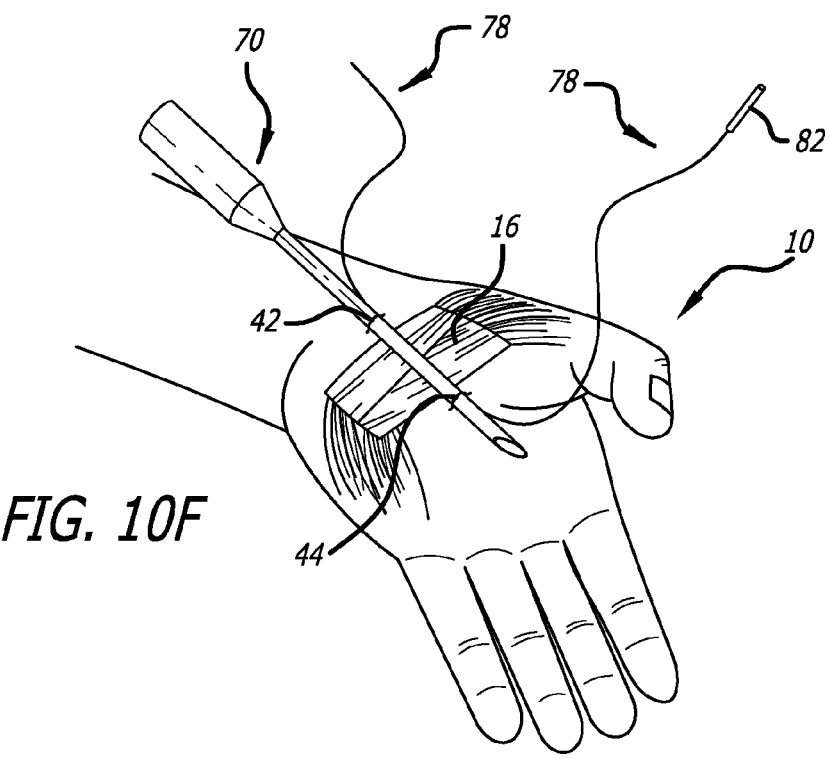
Figure 10G:
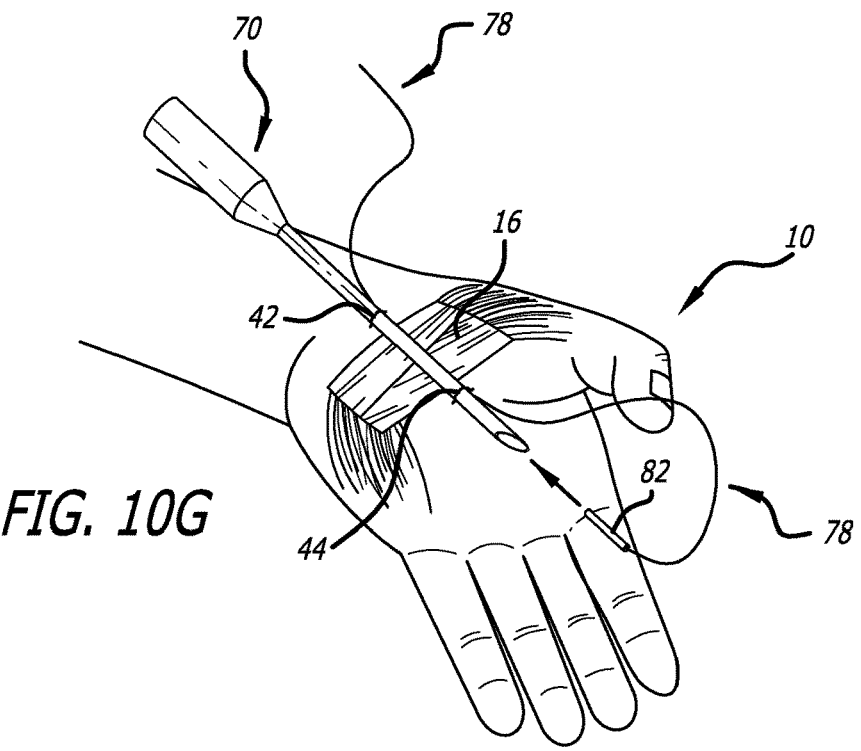

FIG. 10F illustrates the subsequent step of the method wherein the introducer needle has been reintroduced into the hand via entry port 42 immediately adjacent to the placed cutting element 78. The introducer needle has been advanced through the hand immediately above the transverse carpal ligament 16 to reemerge from access port 44. Alternatively, the introducer needle may be reintroduced into the hand via access port 44 to reemerge from port 42.

Figure 10H:
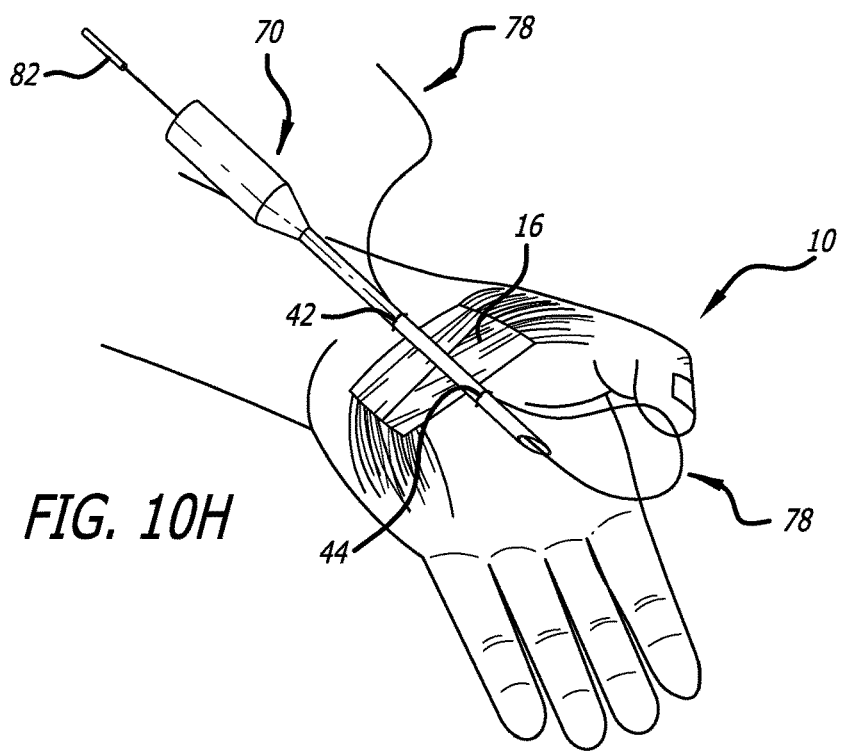
Figure 10I:
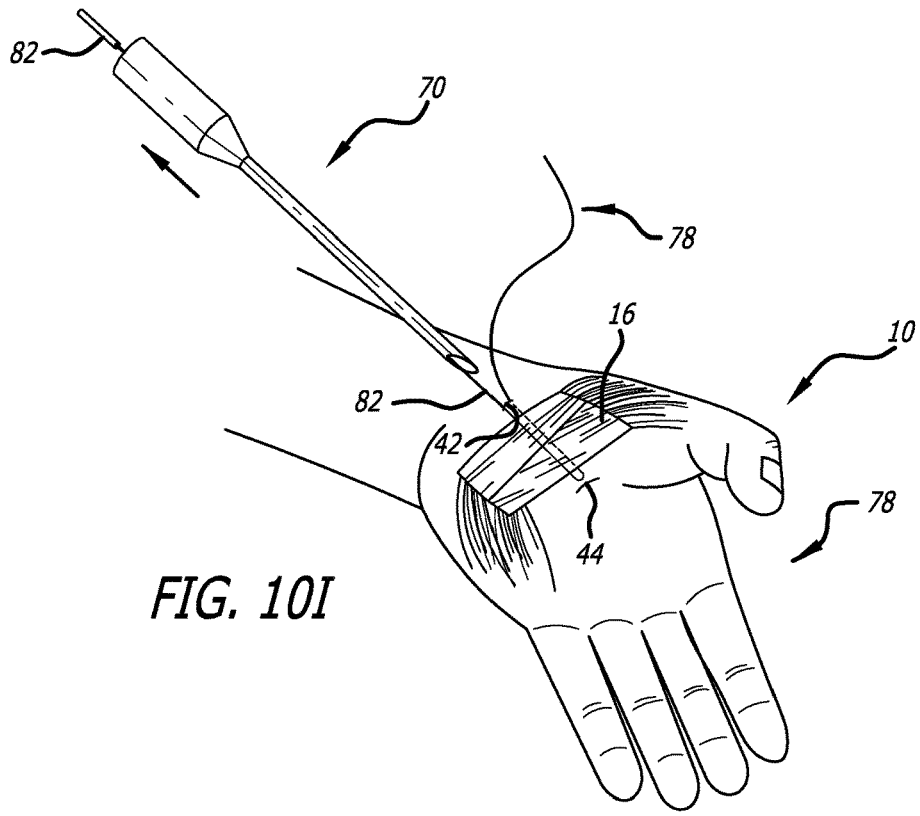
Figure 10J:
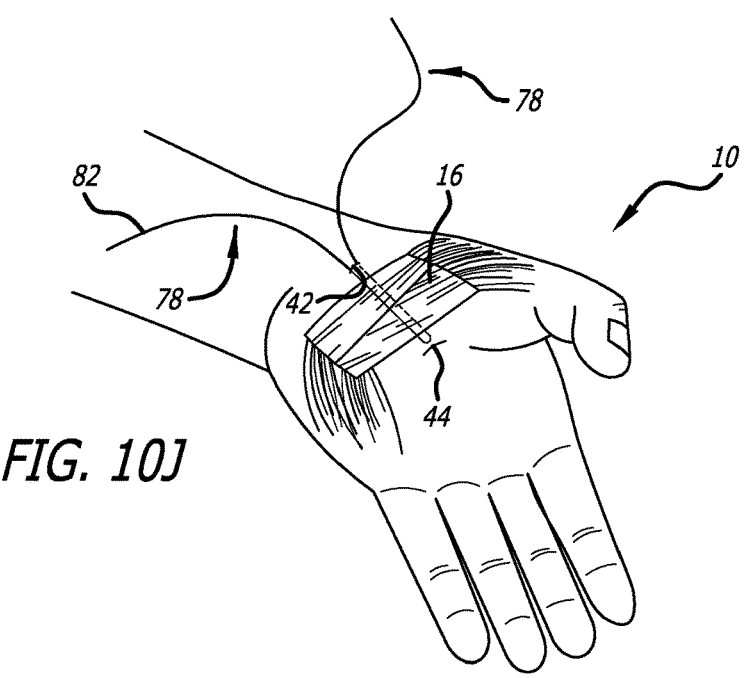

Once the introducer needle 70 is again in place, the cutting element 78 is fed into the distal end of the introducer needle, is extended along the needle's hollow interior to project from its proximal end as is shown in FIG. 10H. Subsequent retraction of the introducer needle as per FIG. 10I leaves the cutting element in position about the ligament 16 as is shown in FIG. 10J. The cutting element is thereby in position for subsequent manipulation to effect the transection of the ligament.

Alternatively, a cutting element having a stiffened section at both ends allows the cutting element to be initially introduced into the distal end of the introducer needle and extended there through. After retraction of the needle and reintroduction into the hand and extension above the ligament to re-emerge from the hand, the second stiffened end of the cutting element can be inserted into the distal end of the needle and extended there through. Subsequent retraction of the needle again leaves the cutting element in position for the transection.

The cutting element may simply be grasped by the user, may be wound around the hands or fingers of the user for a firmer grip or alternatively, may be fitted with handles to provide for maximum grip and control. Unequal forces can alternatingly be applied to the two ends of the cutting element to induce a reciprocating cutting action either by hand or with the use of an appropriately configured power tool. Alternatively, one end can be pulled with greater force than the other element so as to pull the cutting element in a single direction as it cuts through the ligament. As a further alternative, both ends can be pulled simultaneously with equal force to simply pull the cutting element through the ligament. When transection has been achieved, the cutting element is simply withdrawn through access port 42. Application of a small bandage over each of the access ports 42, 44 completes the procedure.

Figure 11:
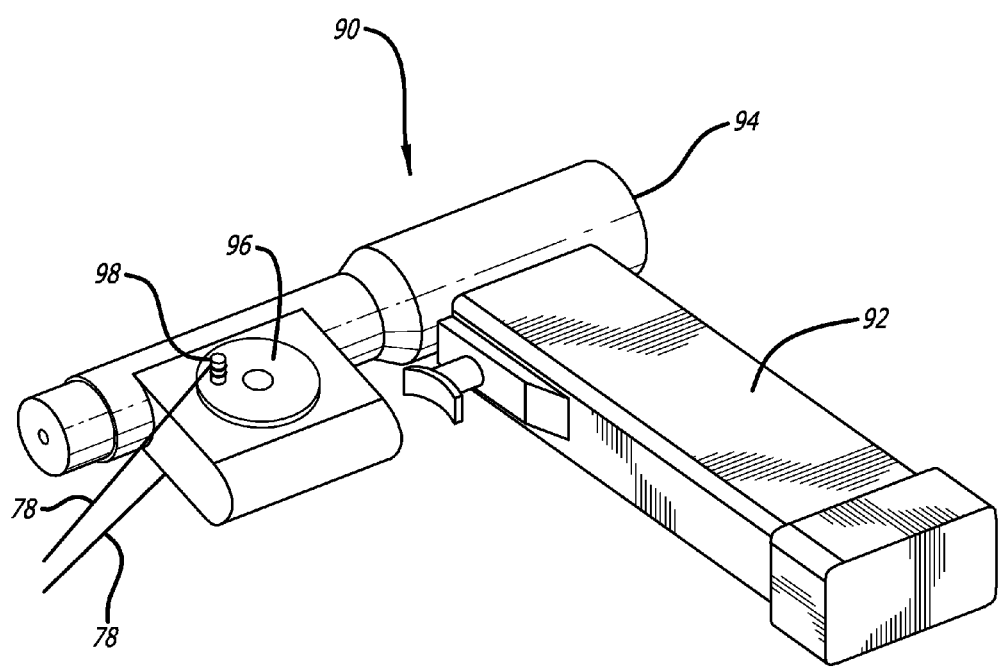
FIG. 11 is a perspective view of a power tool for reciprocating the cutting element once in position about the target ligament.

FIG. 11 generally illustrates a power tool 90 for reciprocating the ends of the cutting element 78. The power tool may include a hand grip section 92, which may house a battery pack. An electric motor would be housed in section 94, rotation of which is mechanically converted to a reciprocating effect. In the embodiment shown, reciprocation is achieved by the rotation of a crankshaft wherein a pin 98 extends from a rotatable disc on each side of the device wherein the pins are diametrically opposed relative one another and to which the ends of the cutting element 78 are attached. Converting the rotation of a longitudinally positioned electric motor to a transversely disposed crankshaft can be achieved in any of various well known ways including for example geared, cammed or desmodromic mechanisms among many others.

Figure 12:
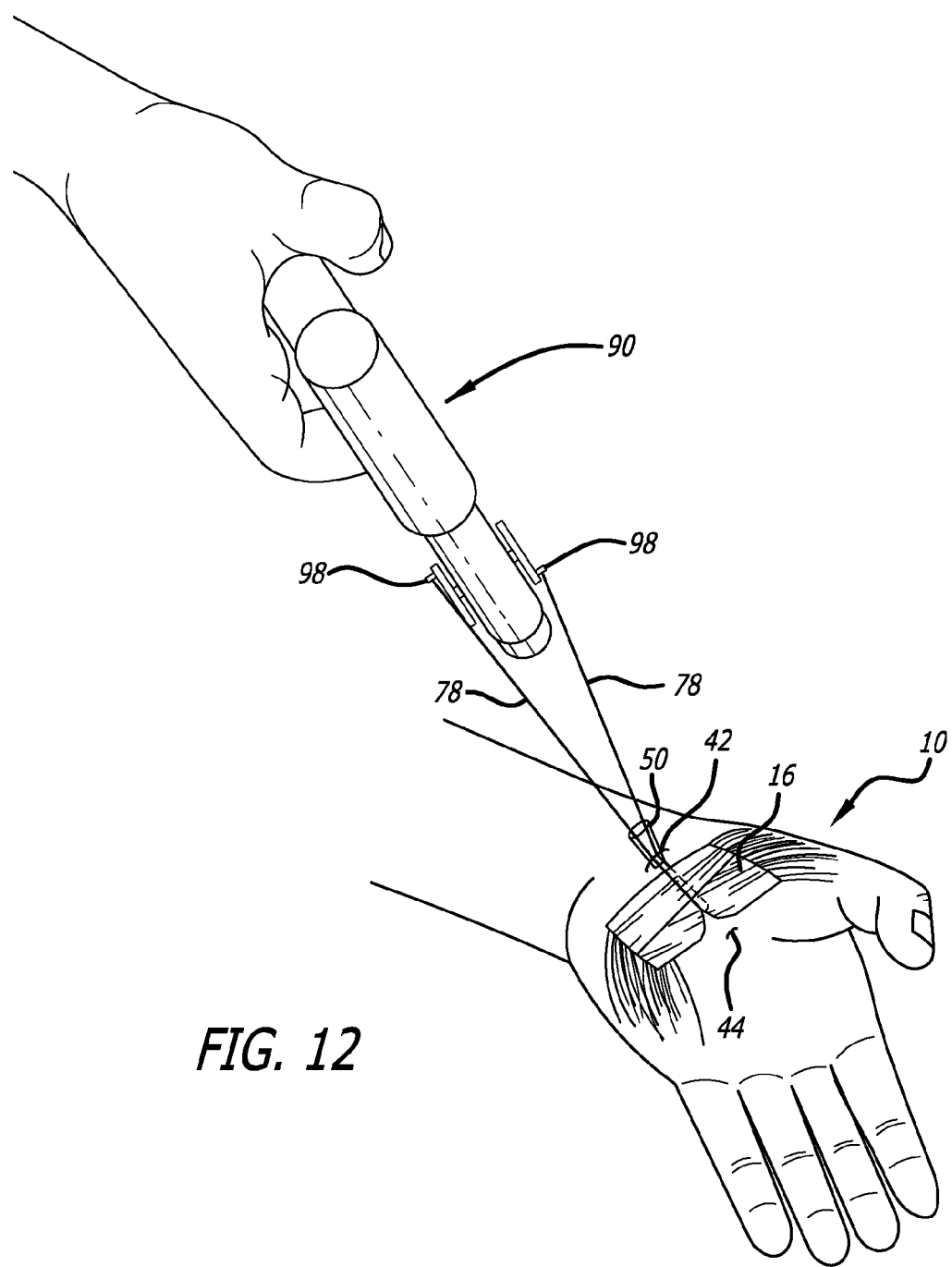
FIG. 12 illustrates the power tool being used to reciprocate the cutting element in place about the ligament.

FIG. 12 illustrates the power tool 90 being used to reciprocate the cutting element 78 in place about the transverse carpal ligament. A protective sleeve 50 may be fitted so as to maintain the two ends of the cutting element in alignment with one another and minimize trauma to the surrounding tissue.

While particular forms of the invention have been described and illustrated, it will also be apparent to those skilled in the art that various modifications can be made without departing from the spirit and scope of the invention. For example, the sequence of steps may be altered so as to cause the retrieval tool to traverse and then retrieve a loop of the cutting element across the top surface of the transverse carpal ligament before traversal of the bottom surface is achieved. Additional access ports may be formed for easier looping of the cutting element. Any of various ports can be used as the final exiting port of the two ends of the cutting element. Additionally, the method and appropriately dimensioned retrieval tool can be used to transect other tissue so as to perform for example, but no limited to, trigger finger release surgery, tarsal tunnel release surgery and plantar fascia release surgery. The apparatus and method can readily be adapted to transect other soft tissue such as for example muscle, tendon, vessels and nerves in humans as well as animals. Accordingly, it is not intended that the invention be limited except by the appended claims.

What is claimed:

1. A method for transecting a soft tissue within a body, comprising the steps of:
    providing a flexible thread-like cutting element having a smooth and non-abrasive cutting surface having an average surface roughness no greater than 50 micrometers;
    providing a hollow introducer needle configured to inject a liquid into the body and having a distal end and a proximal end;
    extending the distal end of the hollow introducer needle into the body at a first location transversely adjacent the soft tissue and out of the body at a second location transversely adjacent to the soft tissue and opposite the first location so as to traverse the soft tissue on a first side, wherein a liquid is injected by and through the hollow introducer needle into the body to separate the soft tissue and provide access for a routing path for the hollow introducer needle;
    extending the cutting element through the proximal end of the hollow introducer needle to leave the cutting element projecting proximally and distally from the hollow introducer needle;
    retracting said the hollow introducer needle from said the body so as to leave the cutting element in place;
    re-extending the distal end of the hollow introducer needle into the body at the first location and out of the body at the second location or into the body at the second location and out of the body at the first location so as to traverse the soft tissue on a second side thereof opposite the first side, wherein liquid is injected by and through the introducer needle into the body to provide space for the extension of the hollow introducer needle;
    extending the end of the cutting element at the same side with the distal end of the needle through the distal end of the hollow introducer needle such that the first end of the cutting element projects from the proximal end of the hollow introducer needle;
    retracting the hollow introducer needle from the body to thereby leave the cutting element in place looped about the soft tissue with the both ends of the cutting element extending from the same location of the body; and
    exerting force on the ends of the cutting element so as to achieve a kerf-less transection of the soft tissue by the smooth and non-abrasive cutting surface of the cutting element.

2. The method of claim 1, wherein unequal forces are exerted on the ends of the cutting element to alternately pull the cutting element in opposite directions to transect the soft tissue.

3. The method of claim 2, further comprising the steps of providing a powered hand tool for alternately reciprocating ends of a cutting element and attaching the projecting ends thereto.

4. The method of claim 1, wherein unequal forces are exerted on the ends of the cutting element so as to pull the cutting element in a single direction to transect the soft tissue.

5. The method of claim 1, wherein substantially equal forces are simultaneously exerted on both ends of the cutting element to transect the soft tissue.

6. The method of claim 1, further providing an ultrasound imaging device for visualizing the extensions of the hollow introducer needle within the body.

7. The method of claim 1, further comprising the step of positioning a protective tube about both end portions of the cutting element projecting from the body.

8. The method of claim 1, wherein the soft tissue comprises a ligament.

9. The method of claim 8, wherein the ligament comprises the transverse carpal ligament.

* * * * *